United States Patent
Seto et al.

(10) Patent No.: US 6,468,801 B2
(45) Date of Patent: Oct. 22, 2002

(54) METHOD OF JUDGING PRESENCE OF FRAMELESS CHEMICAL ANALYSIS FILM IN CHEMICAL ANALYSIS FILM CARTRIDGE

(75) Inventors: Yoshihiro Seto; Shunichi Seto, both of Kanagawa-ken; Osamu Seshimoto, Saitama-ken, all of (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/867,725

(22) Filed: May 29, 2001

(65) Prior Publication Data

US 2001/0024832 A1 Sep. 27, 2001

Related U.S. Application Data

(63) Continuation of application No. 08/399,163, filed on Mar. 2, 1995, now abandoned.

(30) Foreign Application Priority Data

Mar. 11, 1994 (JP) ................................................ 4-40194

(51) Int. Cl.[7] ............................................... G01N 35/00
(52) U.S. Cl. ............................... 436/46; 422/63; 436/50
(58) Field of Search .............................. 436/43, 46, 47, 436/48, 50, 55; 422/63, 64, 65, 67, 105, 107, 108, 119

(56) References Cited

U.S. PATENT DOCUMENTS 5,075,079 A * 12/1991 Kerr et al.
5,314,825 A * 5/1994 Weyrauch et al.

FOREIGN PATENT DOCUMENTS

EP 0555654 A2 * 8/1993

* cited by examiner

*Primary Examiner*—Jan Ludlow
(74) *Attorney, Agent, or Firm*—Reed Smith LLP

(57) ABSTRACT

Whether or not there remains a frameless chemical analysis film in a cartridge in which a plurality of the frameless chemical analysis films are stacked is judged by a film presence detector disposed in a second position different from a position where a film takeout mechanism takes out the frameless chemical analysis films from the cartridge so that the film presence detector does not interfere with the film takeout mechanism.

1 Claim, 14 Drawing Sheets

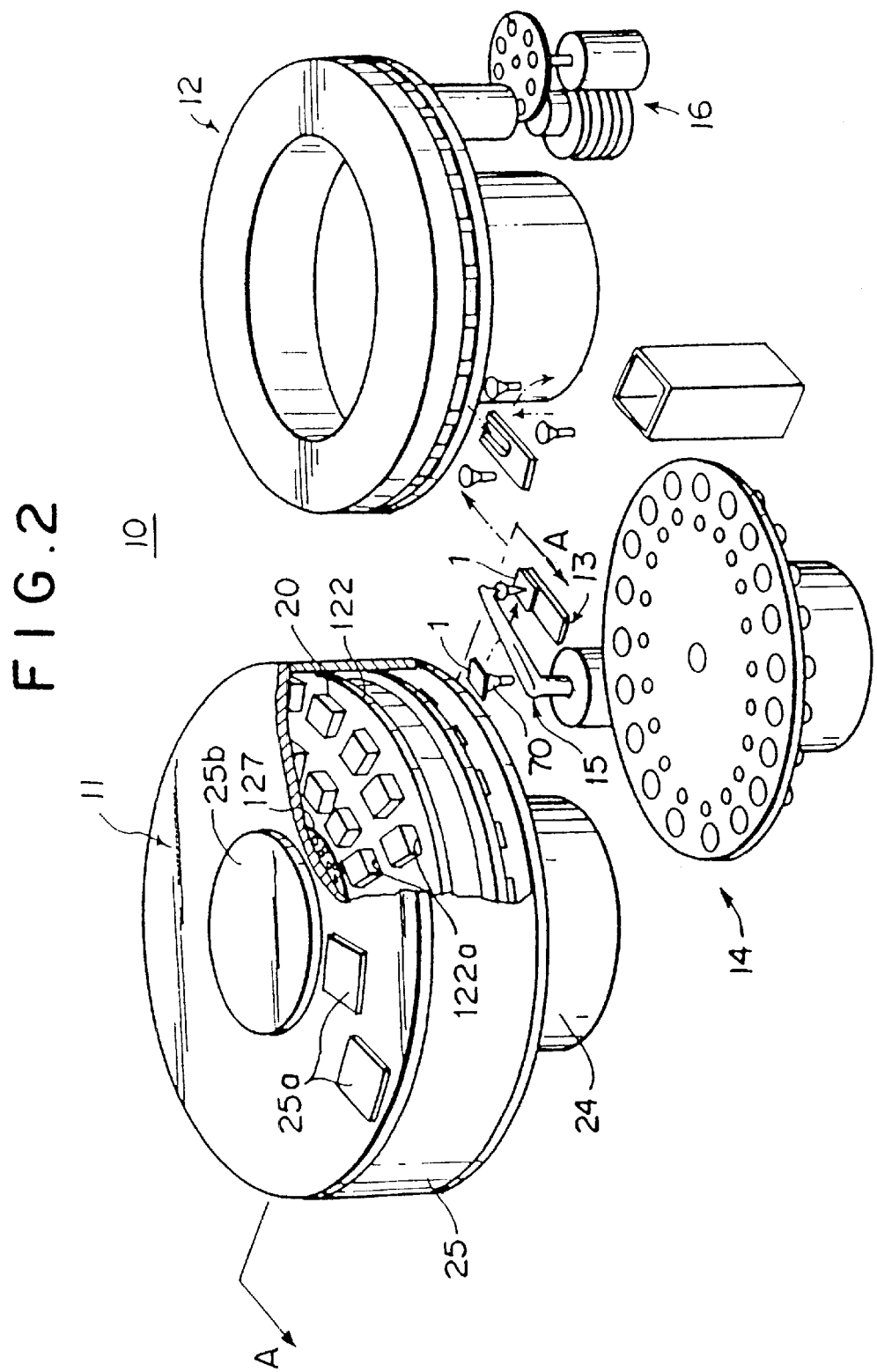

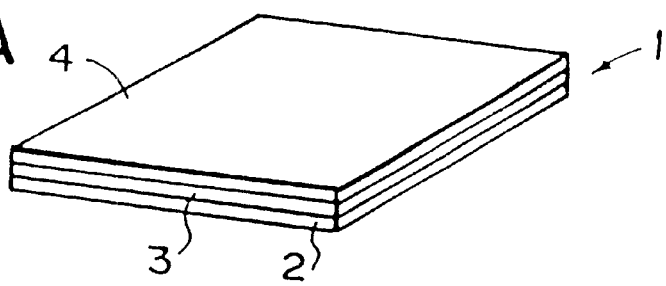
F I G. 3A
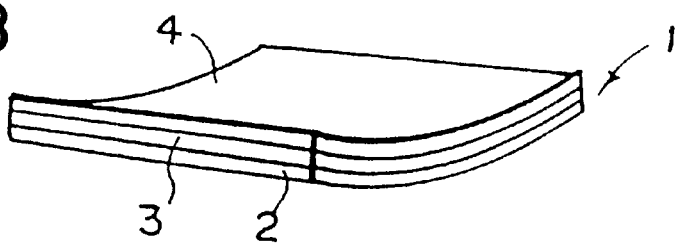
F I G. 3B
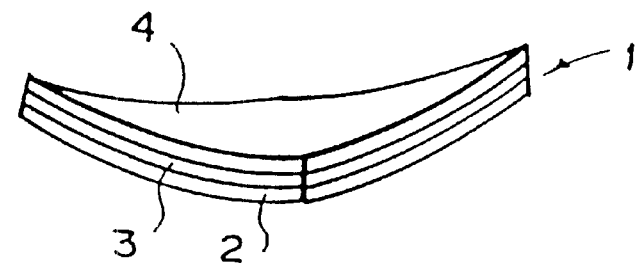
F I G. 3C

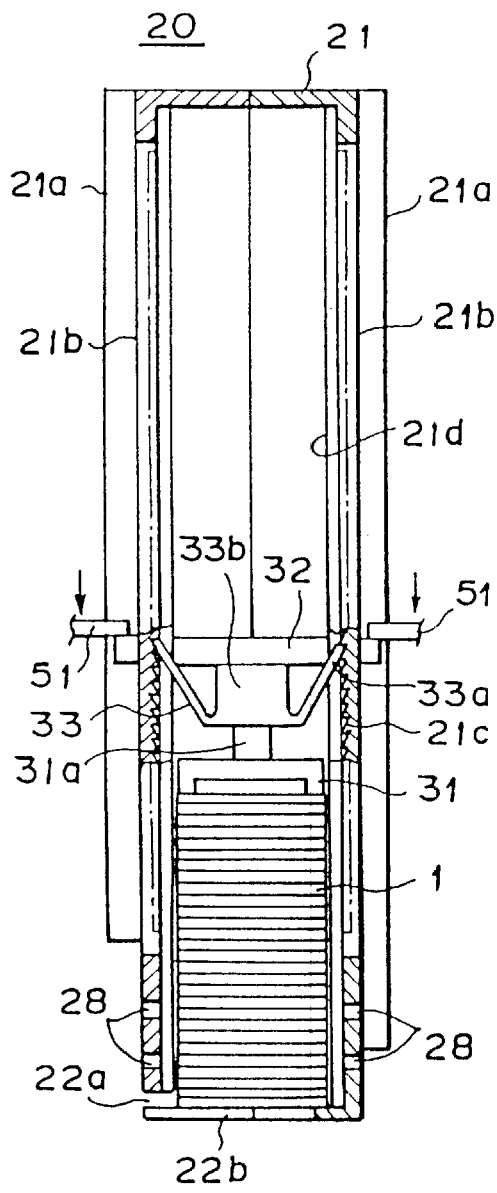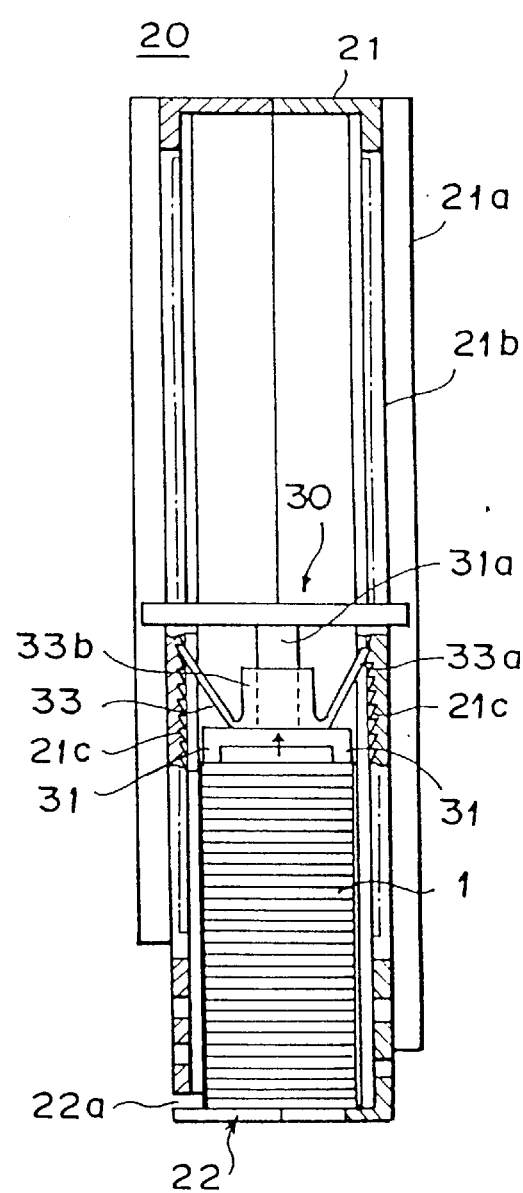

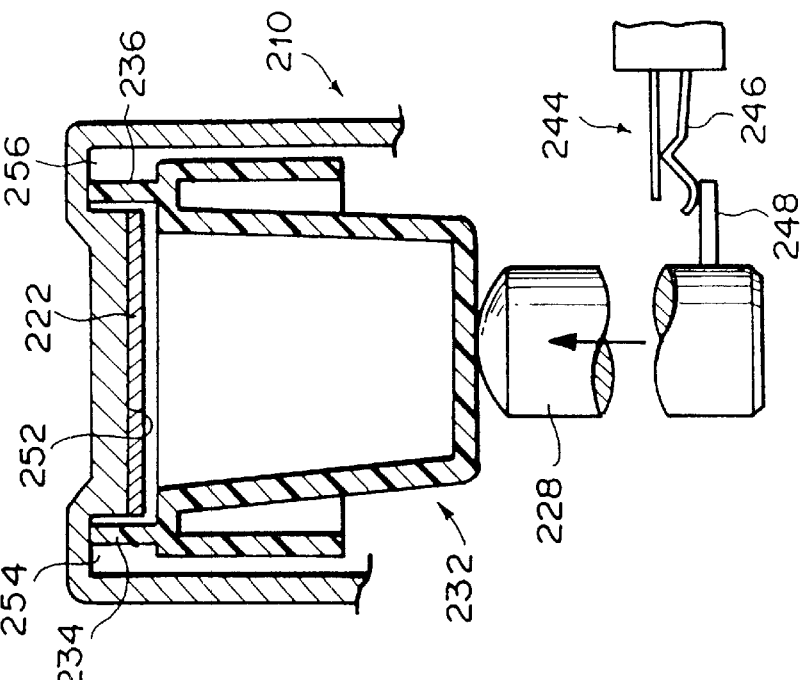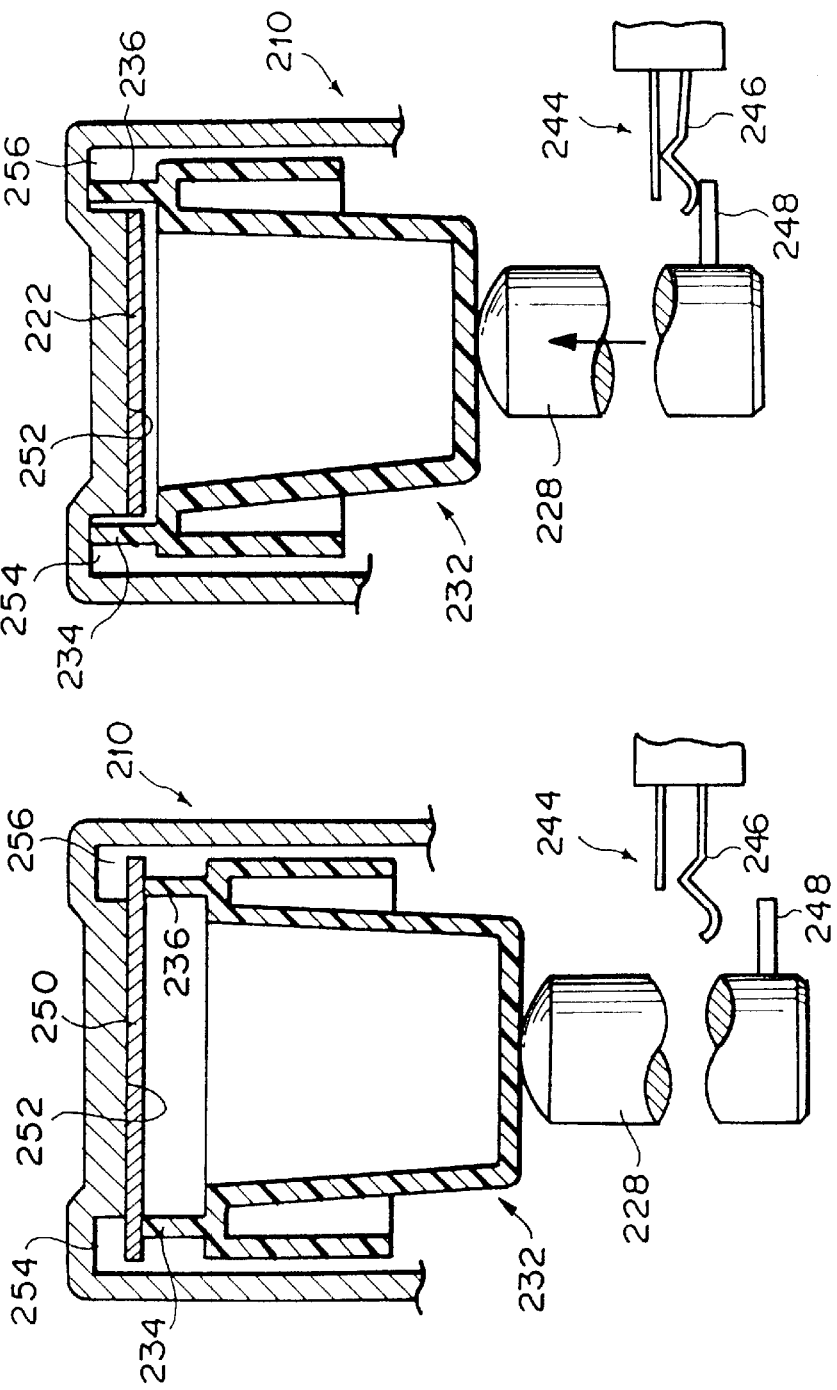

METHOD OF JUDGING PRESENCE OF FRAMELESS CHEMICAL ANALYSIS FILM IN CHEMICAL ANALYSIS FILM CARTRIDGE

CROSS-REFERENCE TO RELATED APPLICATIONS

This application is a continuation application of U.S. patent application Ser. No. 08/399,163 filed on Mar. 2, 1995 now abandoned and entitled METHOD OF JUDGING PRESENCE OF FRAMELESS CHEMICAL ANALYSIS FILM IN CHEMICAL ANALYSIS FILM CARTRIDGE.

BACKGROUND OF THE INVENTION

1. Field of the Invention

This invention relates to a method of judging presence of a frameless chemical analysis film in a cartridge, and more particularly to a method of judging whether there remains a frameless chemical analysis film in a cartridge in which a plurality of chemical analysis films are stored in a stack. The frameless chemical analysis film (including biochemical anlysis films and immunological anlysis films) is a film chip carrying thereon a reagent layer containing a reagent whose optical density changes through a chemical reaction, a biochemical reaction, an immunoreaction (immunological or immunochemical reaction) or the like with a specific biochemical component contained in a sample liquid such as blood or urine.

2. Description of the Prior Art

Quantitative or qualitative analysis of a specific component in a sample liquid is a common operation carried out various industrial, medical and clinical fields. Especially, quantitative analysis of a chemical or biochemical component or a solid component contained in body fluid such as blood or urine is very important in the field of clinical biochemistry.

There has been put into practice a "dry-to-the-touch" chemical or biochemical analysis film with which a specific component contained in a sample liquid can be quantitatively analyzed through a droplet of the sample liquid spotted on the slide. See Japanese Patent Publication No. 53(1978)-21677, (U.S. Pat. No. 3,992,158), Japanese Unexamined Patent Publication No. 55(1980)-164356, (U.S. Pat. No. 4,292,272) or the like. When such a dry chemical analysis film is used, the sample liquid can be analyzed more easily and more quickly than when the conventional wet analysis method is used, and accordingly the dry chemical analysis film is very convenient for medical facilities, laboratories and the like where lots of sample liquids have to be analyzed.

In a biochemical analysis apparatus for quantitatively analyzing chemical components or the like contained in a sample liquid using such a dry chemical analysis film, a droplet of the sample liquid is spotted on the film and is held at a constant temperature for a predetermined time (incubation) in an incubator so that coloring reaction adequately occurs, and the optical density of the color formed by the coloring reaction is optically measured. That is, measuring light containing a wavelength which is preselected according to the combination of the component to be analyzed and the reagent contained in the reagent layer of the film is projected onto the film and the optical density of the film is measured. Then the component to be analyzed is calculated on the basis of the optical density using a standard curve which represents the relation between the concentration of the biochemical component and the optical density. Thereafter the film is taken out from the incubator and discarded into a discarding box.

The chemical analysis film is generally composed of a support sheet of an organic polymer or the like and a reagent layer and a spreading layer formed on the support sheet and is conventionally generally provided with a plastic frame which holds the chemical analysis film flat which is apt to warp into a roof tile shape when it keeps in dried conditions. The chemical analysis film with frame is generally referred to as "chemical analysis slide". However, the frame increases the volume and the size of the chemical analysis film and results in increase in the size of various parts handling the film such as cells in the incubator for incubating the chemical analysis films, the film transfer system, the film supplier for storing the films, the film cartridges and the like. Thus the frame of the chemical analysis film is obstructive to reducing the size of the biochemical analysis apparatus and at the same time reduces the film accommodating capacity of the incubator, which obstructs increase in handling capability of the overall biochemical analysis apparatus. Further the cost of mounting the frame is high, which adds to the cost of biochemical analysis.

In a biochemical analysis apparatus we have proposed previously, the film chip is used as it is without frame (will be referred to as "frameless chemical analysis film", hereinbelow). For example, in the biochemical analysis apparatus disclosed in Japanese Unexamined Patent Publication No. 5(1993)-188058 (corresponding to EP 0 555 654A2) or Japanese Unexamined Patent Publication No. 6(1994)-213903 (corresponding to EP 0 567 067A), a plurality of the frameless chemical analysis films are loaded in a cartridge and are taken out from the cartridge by means of an attracting means such as a reduced pressure suction cup in order to prevent damage to the film.

In such a biochemical analysis apparatus, a plurality of cartridges in which different types of frameless chemical analysis films (films for different analytes: biochemical components to be analyzed) are stored are set in the apparatus. When an analyte is designated, one of the cartridges in which frameless chemical analysis films corresponding to the analyte are stored is set to a film takeout position, the attracting means is moved to the film takeout position and then suction force (reduced pressure) is applied to the attracting means to attract one of the frameless chemical analysis films in the cartridge which is nearest to the film takeout position. Thereafter the attracting means is moved in a predetermined direction while holding the frameless chemical analysis film under the suction force to take out the film through a film takeout port in the cartridge. These operations are automatically carried out according to a predetermined program stored in the biochemical analysis apparatus.

When there remains no film in the cartridge set to the film takeout position, the series of the operations for taking out the film becomes vain, which deteriorates analyzing efficiency of the apparatus. Accordingly it is preferred that whether there remains some films in the cartridge be detected in advance and when no film remains in the cartridge, the operations for taking out the film from the cartridge be abandoned and the operations for taking out the film from another cartridge be effected immediately while alarming the operator absence of film (that there remains no film in the cartridge) by means of a buzzer, a lamp, a display or the like.

As disclosed in U.S. Pat. No. 4,190,420, there has been known a system in which whether there remains some chemical analysis slides in a cartridge is judged by means of a limit switch. That is, as shown in FIGS. 16A and 16B, a plurality of chemical analysis slides 250 (though only one slide is shown in FIG. 16A) are stacked in a cartridge 210 and a pressing member 232 is received in the cartridge 210 to be movable up and down in the cartridge 210. When a slide 250 is to be taken out, the pressing member 232 is pushed upward by a plunger 228 and presses the stack of the slides against the inner surface of a support portion 252 which projects downward from the top wall of the cartridge, thereby bringing the uppermost slide to a slide exit port (not shown) formed in a side wall of the cartridge 210. (FIG. 16A) In this state, the uppermost slide 250 is pushed transversely by a blade 222 through the slide exit port whose width is slightly larger than the thickness of the slide 250.

The width of the blade 222 is smaller than that of the slide 250 and the space between abutment edges 234 and 236 of the pressing member 232 is smaller than the width of the slide 250 and larger than the width of the blade 222 and the width of the support portion 252. Accordingly when the last slide 250 is pushed out of the cartridge 210, the abutment edges 234 and 236 of the pressing member 232 are moved upward beyond the lower surface of the support portion 252 into the spaces 254 and 256 between the support portion 252 and the side wall of the cartridge to abut against the bottoms of the spaces 254 and 256 as shown in FIG. 16B. In response to the upward movement of the pressing member 232, the plunger 228 moves upward and a pin 248 projecting from the side of the plunger 228 pushes upward a contact 246 of a limit switch 244 to turn on the limit switch 244. When the limit switch 244 is turned on, an alarm means such as a buzzer, a lamp or a display is energized to alarm the operator that no slide remains in the cartridge 210.

In the prior art described above, the stack of the slides 250 is pushed upward by the plunger 228 by way of the pressing member 232 in order to surely set the uppermost slide to a position suitable for taking out the slide. Further the slide 250 must be kept pressed by the pressing member 232 so that the abutment edges 234 and 236 are inserted into the spaces 254 and 256 in response to pushing out the last slide. That is, the stack of the slides 250 is pressed under a relatively large pressure in order to surely bring the uppermost slide to the takeout position and to surely detect presence or absence of the slide.

As a result, substantially the same portions of the stack of the slides are subjected to a large pressure by the abutment edges 234 and 236 every time the uppermost slide is taken out.

In the case of the chemical analysis slide 250, the chemical analysis film itself is not so damaged so long as the abutment edges 234 and 236 are brought into abutment against the frame of the slide 250.

However when the system of the prior art is applied to the frameless chemical analysis films as it is, the abutment edges 234 and 236 are brought into a direct contact with the surface of the lowermost film and the surface of the lowermost film is kept subjected to a large pressure for a long time. Further the films on the lowermost film are indirectly subjected to the pressure. Further since the uppermost film is transversely slid with the stack of the films kept pressed, friction adversely affects the uppermost film when it is taken out.

That is, the film can be bent or folded or peeled under the influence of the friction generated by the pressure. Further when the spreading layer of the film is kept subjected to a large pressure, condition of the spreading layer changes and the sample liquid spreading speed changes, whereby the measuring accuracy can deteriorate.

In order to overcome such problems, the means for taking out the films and the means for judging presence or absence of the films must be properly arranged and laid out not to interfere with each other.

SUMMARY OF THE INVENTION

In view of the foregoing observations and description, the primary object of the present invention is to provide a method of judging presence of a frameless chemical analysis film in a cartridge in which whether there remains a frameless chemical analysis film can be judged without fear of damaging the film and the means for carrying out the method can be disposed without being restricted by the means for taking out the film.

In accordance with the present invention, there is provided a method of judging presence of a frameless chemical analysis film in a cartridge in which a plurality of the frameless chemical analysis films are stacked, characterized in that whether or not there remains a frameless chemical analysis film in the cartridge is detected by a film presence detecting means disposed in a second position different from a first position where a film takeout means takes out the frameless chemical analysis films from the cartridge so that the film presence detecting means does not interfere with the film takeout means.

It is preferred that the film presence detecting means detects whether or not there remains a frameless chemical analysis film in the cartridge in the second position with the frameless chemical analysis films pressed toward a film takeout port under a force which is not larger than a force required to make the frameless chemical analysis films completely flat.

In accordance with the method of the present invention, whether or not there remains a frameless chemical analysis film in the cartridge is detected in a position different from a position where the frameless chemical analysis films are taken out from the cartridge.

That is, the frameless chemical analysis films are taken out from the cartridge in the first position by a film takeout system using, for instance, a vacuum (reduced pressure) attracting means.

Since the vacuum attracting means is moved outside the film takeout port in the vicinity thereof, it is difficult to dispose the film presence detecting means near the film takeout port.

Accordingly, in accordance with the method of the present invention, the second position where whether or not there remains a frameless chemical analysis film in the cartridge is detected is spaced from the first position where the film takeout means takes out the frameless chemical analysis films from the cartridge, and the film presence detecting means is disposed in the second position.

When the frameless chemical analysis films are pressed toward the film takeout port, the films which are apt to be variously curled or warped in the dry state are reshaped into a substantially uniform shape, whereby accuracy in detecting whether there remains a film in the cartridge can be improved without being affected by curl or warp of the films.

When the force under which the films are pressed is not larger than a force required to completely remove the curl or warp of the frameless chemical analysis films and render them completely flat, the films can be taken out without damage on the surfaces thereof unlike in the aforesaid prior art where the slides are pressed under a large force when they are taken out.

BRIEF DESCRIPTION OF THE DRAWINGS

FIG. 2 is a schematic perspective view of the biochemical analysis apparatus, FIGS. 3A to 3C are perspective views respectively showing the structure of the frameless chemical analysis film in different conditions, FIGS. 7A and 7B are cross-sectional views for illustrating the operation of the engagement member and the pressing member.

DESCRIPTION OF THE PREFERRED EMBODIMENTS

Figure 1:
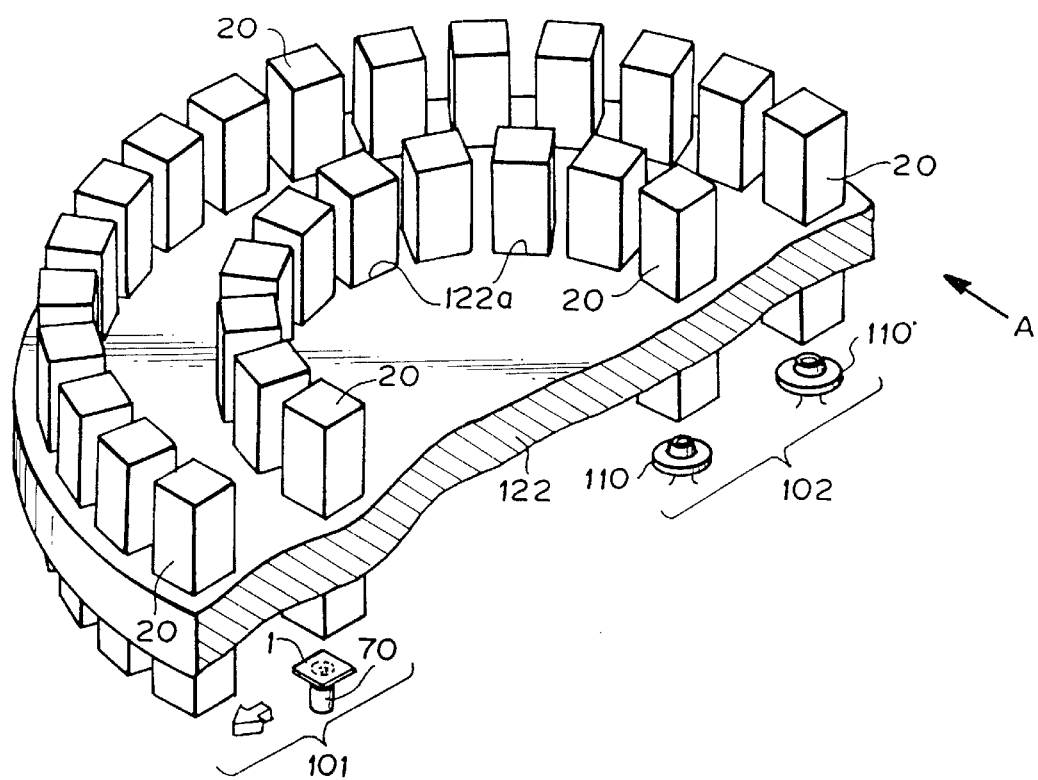
FIG. 1 is a fragmentary schematic view showing a part of a biochemical analysis apparatus to which the method of the present invention is applied.
Figure 4:
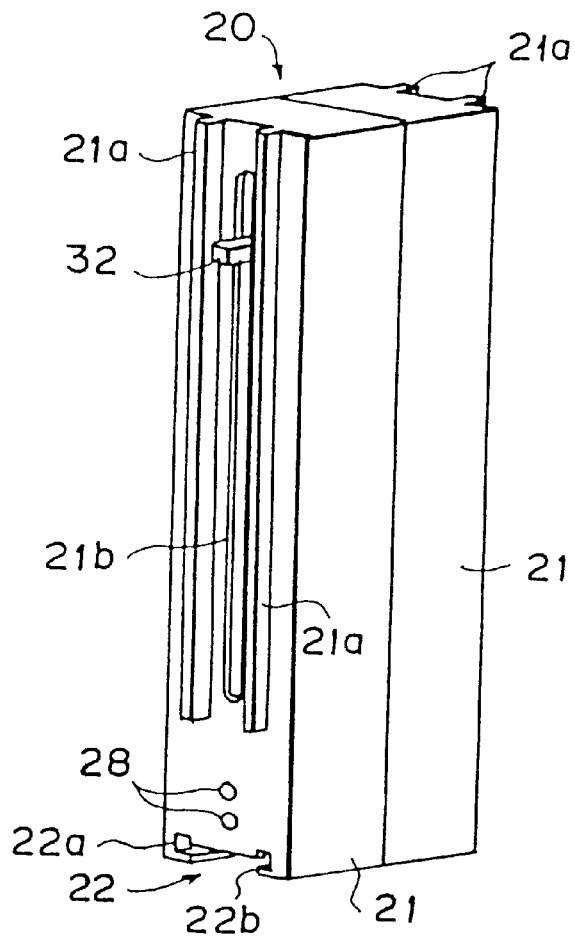
FIG. 4 is a perspective view of the cartridge.
Figure 5:
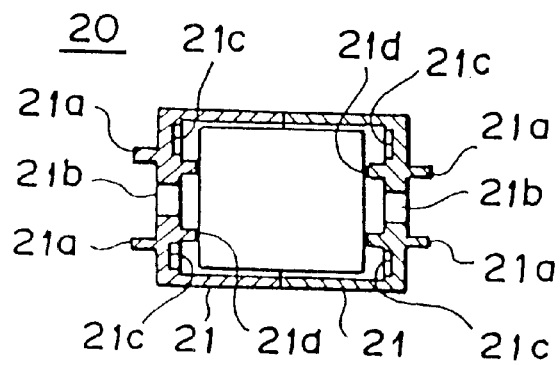
FIG. 5 is a cross-sectional view of the cartridge with the pressing member removed.

In FIG. 2, a biochemical analysis apparatus 10 comprises a film supplier 11 in which a plurality of virgin rectangular (or nearly square) frameless chemical analysis films 1 are stored, an incubator 12 which is disposed beside the film supplier 11 and incubates the frameless chemical analysis films 1 at a predetermined temperature for a predetermined time, a film transfer means 13 which transfers the frameless chemical analysis films 1 from the film supplier 11 to the incubator 12, a sample liquid supplier 14 in which a plurality of sample liquids such as serum, urine or the like are stored, a spotting mechanism 15 which spots one of the sample liquids in the sample liquid supplier 14 on the frameless chemical analysis film 1 on the way to the incubator 12, and a light measuring system 16 disposed below the incubator 12.

As shown in FIG. 3A, the frameless chemical analysis film 1 comprises a light-transmissive support sheet 2 formed of plastic film such as polyethylene terephthalate, polystyrene or the like, a reagent layer 3 and a spreading layer 4. That is, the frameless chemical analysis film 1 is formed by coating or bonding the reagent layer 3 on the support sheet 2 and laminating the spreading layer 4 on the reagent layer 3. It should be noted that the film is not provided with any frame.

The reagent layer 3 comprises at least one layer composed of a hydrophilic polymer binder (e.g., gelatin) or a porous layer (e.g., filter paper, cloth, microporous polymer sheet) containing therein a detecting reagent component which specifically reacts with an analyte (a chemical, biochemical or immunochemical component to be analyzed) and a reagent component (chemical analysis reagent or immunoassay reagent) which is necessary for coloring reaction.

The spreading layer 4 is formed of a material resistant to rubbing, such as woven, unwoven or knitted fabric (or cloth) of synthetic fiber such as polyester or of blend of natural fiber and synthetic fiber, or paper and functions as a protective layer. Further the spreading layer 4 causes sample liquid applied thereto to uniformly spread over the reagent layer 3.

Under the normal humidity conditions the frameless chemical analysis film 1 is substantially flat as shown in FIG. 3A. The film 1 is stored in a dry environment (e.g., in an environment where the humidity is not higher than 20%) in order to suppress chemical reaction or immunoreaction, and in a dry state, the film 1 is warped (curled or curved) toward the spreading layer 4 as shown in FIG. 3B or 3C.

The chemical analysis films 1 are stacked in cartridges 20 shown in FIGS. 4 to 7 (7A and 7B) for the respective items of measurement (analytes to be analyzed) with the supports sheets 2 facing downward.

As shown in FIG. 2, a plurality of the cartridges 20 are respectively loaded in a plurality of cartridge holding portions 122a formed in a support member 122 in the film supplier 11. In this particular embodiment, the cartridge holding portions 122a are arranged on inner and outer circles. The support member 122 is rotated by a supplier motor (not shown) provided in a base portion 24 to bring a desired cartridge 20 to a film takeout position where the film transfer means 13 takes out the film 1 in the cartridge 20.

The film supplier 11 is provided with a cover 25 which tightly encloses the inner space of the film supplier 11. The cover 25 is provided with a pair of openings 25a provided with lids and the cartridges 20 are taken out and inserted into the cartridge holding portions through the openings 25a. An dehumidifying agent holding portion 127 is formed in the support member 122 at the center thereof and dehumidifying agent (desiccant) is loaded in the dehumidifying agent holding portion 127 through an opening 25b formed in the cover 25. The opening 25b is provided with a lid. Thus the inner space of the film supplier 11 is kept within a predetermined humidity range.

A shutter (not shown) is provided in the lower surface of the film supplier 11 in the film takeout position. The shutter is opened when the film 1 is taken out from the cartridge 20 and a suction pad 70 of the film transfer means 13 takes out the lowermost film 1 in the cartridge 20 through the shutter.

As shown in FIGS. 4 to 7 (7A and 7B), the cartridge 20 comprises a box-like cartridge body 21. The cartridge body 21 is rectangular in cross-section and is divided into left and right halves along a vertical plane at the center thereof. The cartridge body 21 is provied with a film takeout port 22 in one side near the bottom thereof. The film takeout port 22 comprises a first opening 22a which opens in one side of the cartridge body 21 and permits only one film 1 to pass therethrough and a second opening 22b which opens in the bottom of the cartridge body 21 and gives access to the lowermost film of the stack of the films 1 to a suction pad 70 which attracts the lowermost film 1 and holds it under a suction force.

A pair of outer ribs 21a are formed on each of the left and right side walls of the cartridge body 21 to extend in the longitudinal direction of the cartridge body 21. The space between the outer ribs 21a on the left side wall differs from that on the right side wall to prevent insertion of the cartridge 20 into the film supplier 11 in a wrong position. The outer ribs 21a project in the transverse direction of the cartridge body 21 beyond the ends of an external force receiving portion 32 of a film feed mechanism 30 (to be described later) which project from the cartridge body 21 in the transverse direction thereof between the outer ribs 21a and protect the ends of the external force receiving portion 32. Further the outer ribs 21a reinforce the cartridge body 21.

In each of the left and right side walls, a longitudinal slit 21b is formed to extend in the longitudinal direction of the cartridge body 21 between the outer ribs 21a, and a pair of inner ribs 21d are formed on the inner surface of each of the left and right side walls to extend in the longitudinal direction of the cartridge body 21 on opposite sides of the longitudinal slit 21b. Ratchet teeth 21c are formed on the inner surface of each of the left and right side walls to extend along the inner ribs 21d on opposite sides of the inner ribs 21d.

The thickness of the chemical analysis films 1 can differ depending on the analytes to be analyzed and the size of the first opening 22a is set depending on the thickness of the films 1 to be loaded in the cartridge 20 so that the films 1 can be taken out surely one by one through the first opening 22a. In order to check the compatibility of each cartridge body 21 with the films 1 to be loaded therein, distinguishing holes 28 are selectively formed in the left and right side walls. That is, a pair of holes 28a are formed in the left side wall arranged in a vertical direction and no or one or two holes are formed in the right side wall. When one hole is formed in the right side wall, the single hole is formed to be aligned with the upper or lower hole in the left side wall. When two holes are formed in the right side wall, the two holes are formed to be aligned respectively with the upper and lower holes in the left side wall. Detecting light is projected into the holes 28a in the left side wall toward the right side wall and light passing through the holes 28a is received on the right side of the cartridge body 21 by upper and lower photodetectors (not shown). Thus by combinations of the holes 28a formed in the left and right side walls, four thicknesses of the films 1 to be loaded in the cartridge body 21 can be represented, i.e., one for the case where two holes are formed in the right side wall and the detecting light is received by both the upper and lower photodetectors, another for the case where one hole is formed in the right side wall in alignment with the upper hole in the left side wall and the detecting light is received by only the upper photodetector, another for the case where one hole is formed in the right side wall in alignment with the lower hole in the left side wall and the detecting light is received by only the lower photodetector and the other for the case where no hole is formed in the right side wall and the detecting light is received by none of the upper and lower photodetectors.

Figure 6:
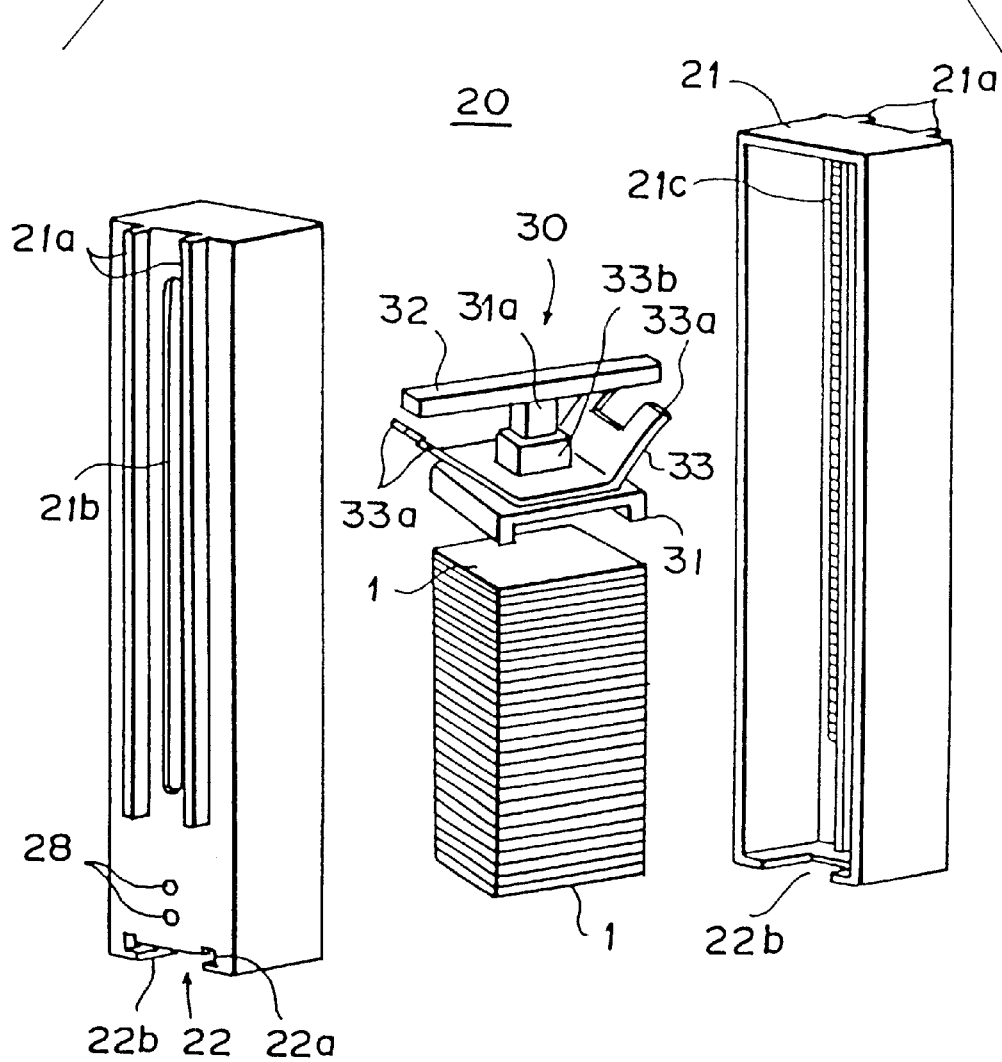
FIG. 6 is an exploded perspective view of the cartridge.

As shown in FIG. 6, a feed mechanism 30 for feeding the stack of the films 1 toward the film takeout port 22 is provided in the cartridge body 21. Since the films 1 are taken out through the film takeout port 22 disposed on the lower end of the cartridge body 21 in this embodiment, the force required to take out the film 1 increases as the urging force is larger, which can result in difficulties in taking out the film 1. In order to overcome this problem, the feed mechanism 30 is provided with a pressing force reducing structure for reducing the film pressing force after the stack of the films 1 is pushed toward the film takeout port 22 in response to one film being taken out from the cartridge. In the structure, a restoring resilient force which is produced when the films 1, which are warped or curled into a roof tile-like shape, are pressed flat is used to reduce the film pressing force. That is, the feed mechanism 30 comprises a pressing member 31, said external force receiving portion 32 and an engagement member 33. The pressing member 31 is brought into contact with the uppermost one of the films 1 in the stack and is shaped to contact with the the uppermost film at edge portions of the film 1, or at corner portions of the same or over entire area of the same. A rod 31a vertically projects upward from the center of the pressing member 31 and the external force receiving portion 32 is formed integrally with the rod 31a to horizontally extend like a bar from the upper end of the rod 31a in T-shape. Though the engagement member 33 is basically moved integrally with the pressing member 31, the engagement member 33 is incorporated in the feed mechanism 30 to be slidable relative to the pressing member 31 by a limited distance along the rod 31a.

Opposite end portions of the external force receiving portion 32 project outside the cartridge body 21 through the longitudinal slits 21b short of the top of the outer ribs 21a. An urging means 50 urges downward the end portions of the external force receiving portion 32 as will be described later.

The engagement member 33 comprises a boss portion 33b which is formed at the center of a plate-like body portion and is slidably fitted on the rod 31a and a pair of resilient claw portions 33a which extend outwardly upward from opposite ends of the plate-like body portion and engage with the ratchet teeth 21c on the inner side of the cartridge body 21 from below. The ratchet teeth 21c are shaped to engage with the claw portion 33a so as to permit the claw portion 33a to move downward relative to the teeth 21c but not to permit the claw portion 33a to move upward relative to the teeth 21c.

Operation of the feed mechanism 30 will be described with reference to FIGS. 7A and 7B, hereinbelow. FIG. 7A shows a state where an actuator member 51 (to be described later) acts on the end portions of the external force receiving portion 32 to push downward the pressing member 31, thereby pushing the stack of the films 1 toward the film takeout port 22. As can be understood from FIG. 7A, when the actuator member 51 pushes downward the external force receiving portion 32, the pressing member 31 moves downward to push the stack of the films 1 toward the film takeout port 22 and presses the stack against the bottom wall of the cartridge body 21, whereby the films 1 are flattened and the stack of the films 1 is compressed. When the pressing member 31 moves downward, the engagement member 33 is left there until the upper end of the boss portion 33b is brought into abutment against the external force receiving portion 32 due to resistance by engagement of the claw portions 33a and the ratchet teeth 21c and thereafter is moved downward together with the pressing member 31 to be brought into engagement with the ratchet teeth 21c at lower portion thereof. In this state, the engagement member 33 is in contact with the external force receiving portion 32 and away from the pressing member 31 as shown in FIG. 7A.

When the external force receiving portion 32 is released from the actuator member 51, the restoring resilient force of the films 1 pushes upward the pressing member 31 and the pressing member 31 is moved upward together with the external force receiving portion 32 until the pressing member 31 is brought into abutment against the bottom of the boss portion 33b of the engagement member 33 which is held stationary by the engagement of the ratchet teeth 21c and the claw portions 33a as shown in FIG. 7B, whereby the pressing force acting on the films 1 is reduced and the film 1 can be easily taken out through the film takeout port 22.

After one film 1 is taken out, the cartridge 20 is moved to a film presence judging position 102 shown in FIG. 1 and the feed mechanism 30 is driven by an urging means 50 (FIGS. 8 and 9) to feed downward the stack of the films 1.

Figure 8:
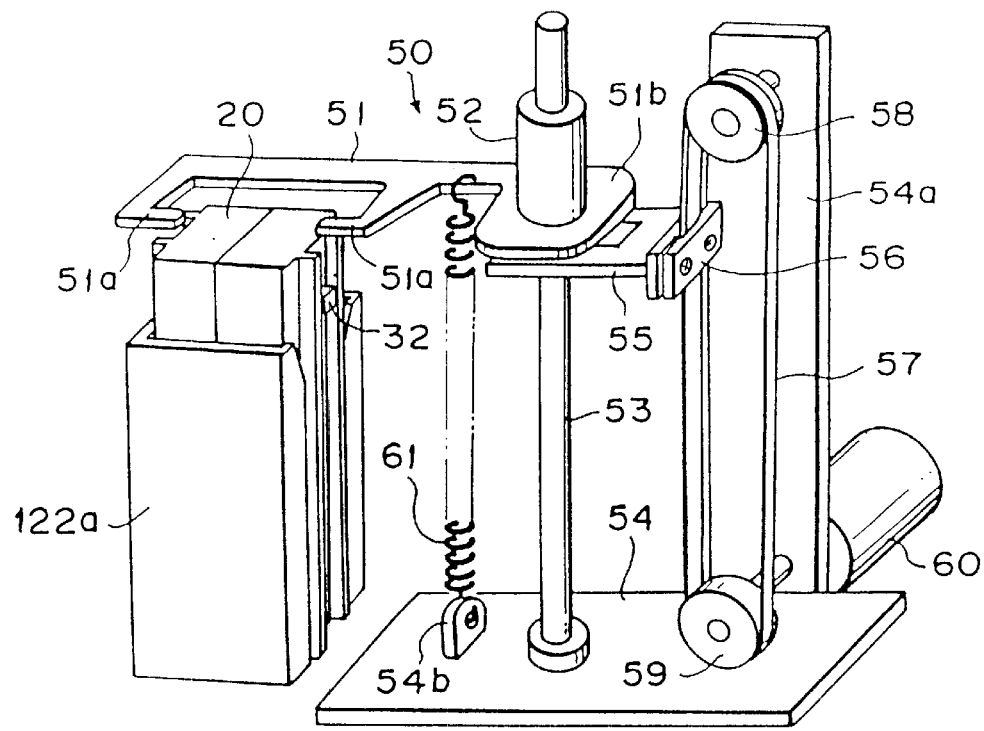
FIG. 8 is a schematic perspective view of the urging means.

An example of the urging means 50 for driving the external force receiving portion 32 of the cartridge 20 will be described with reference to FIGS. 8 and 9, hereinbelow.

The urging means 50 has said actuator member 51 having a pair of engaging end portions 51a which are adapted to be engaged with the external force receiving portion 32 of the cartridge 20. The actuator member 51 is provided with a sliding tube 52 at a base end portion 51b thereof. The sliding tube 52 is slidably fitted on a guide rod 53 stood on a base 54, whereby the actuator member 51 is supported to be movable up and down along the guide rod 53. The base end portion 51b of the actuator member 51 is supported on a support arm 55 which is fixed to a belt 57 by way of a fixing means 56 at one end. The belt 57 is passed around upper and lower pulleys 58 and 59. The lower pulley 59 is driven by a driving motor 60 to move up and down the support arm 55. The actuator member 51 is normally urged downward by a spring 61 provided between a projection 54b of the base 54 and the actuator member 51. The actuator member 51 is held by the support arm 55 against the urging force of the spring 61.

Figure 9:
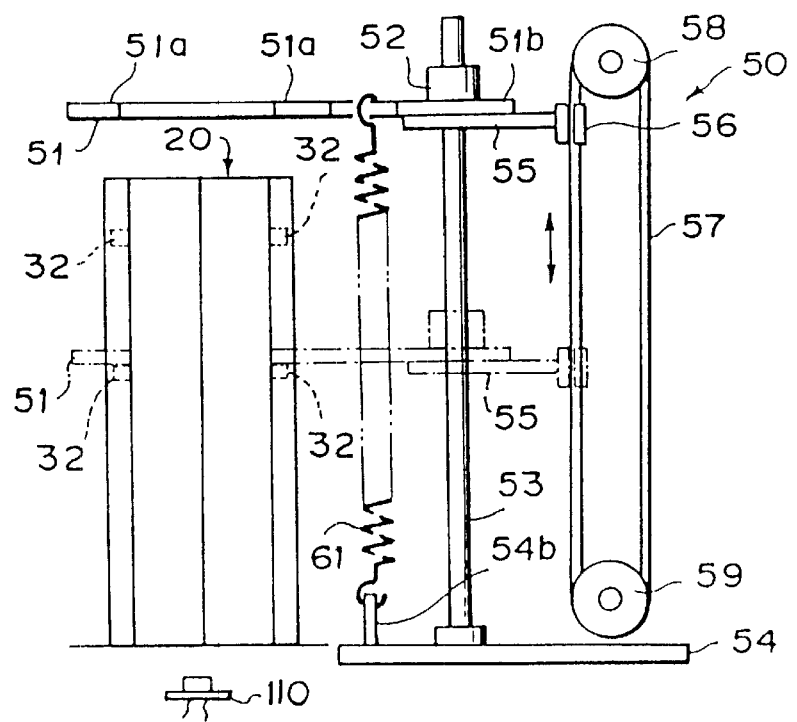
FIG. 9 is a schematic front view of the urging means.

When the support arm 55 is moved downward by the driving motor 60 as shown by the chained line in FIG. 9, the actuator member 51 is moved downward along the guide rod 53 under the force of the spring 61 and the engaging end portions 51a of the actuator member 51 are brought into engagement with the end portions of the external force receiving portion 32, whereby the pressing member 31 presses downward the stack of the films 1 under the force of the spring 61 and feeds it toward the film takeout port 22 as shown in FIG. 7A. After a predetermined pressing, the actuator member 51 is lifted to the position shown by the solid line in FIG. 9 by the driving motor 60 and the external force receiving portion 32 is released from the urging force of the actuator member 51, whereby the pressing force acting on the films 1 is reduced as shown in FIG. 7B. Thereafter another cartridge 20 is brought to the urging means 50 and the similar operation is repeated for the cartridge 20.

As described above, the films 1 in the cartridge 20 are taken out one by one by the suction pad 70. In order to improve the efficiency of the automatic film takeout operation, it is preferred that the operation be started after checking the presence of a film 1 in the cartridge 20. In this embodiment, whether there remains a film 1 in the cartridge 20 is judged in a film presence judging position 102 which is disposed in a position different in space from the film takeout position 102, and then whether the film takeout operation is to be effected is judged on the basis of the result of the judgment.

That is, as shown in FIG. 1, the film presence judging position 102 is disposed below the support member 122 to be opposed to the bottom of one of the cartridges 20 in a position diametrically opposed to or spaced by 180° from the film takeout position 101.

Figure 10:
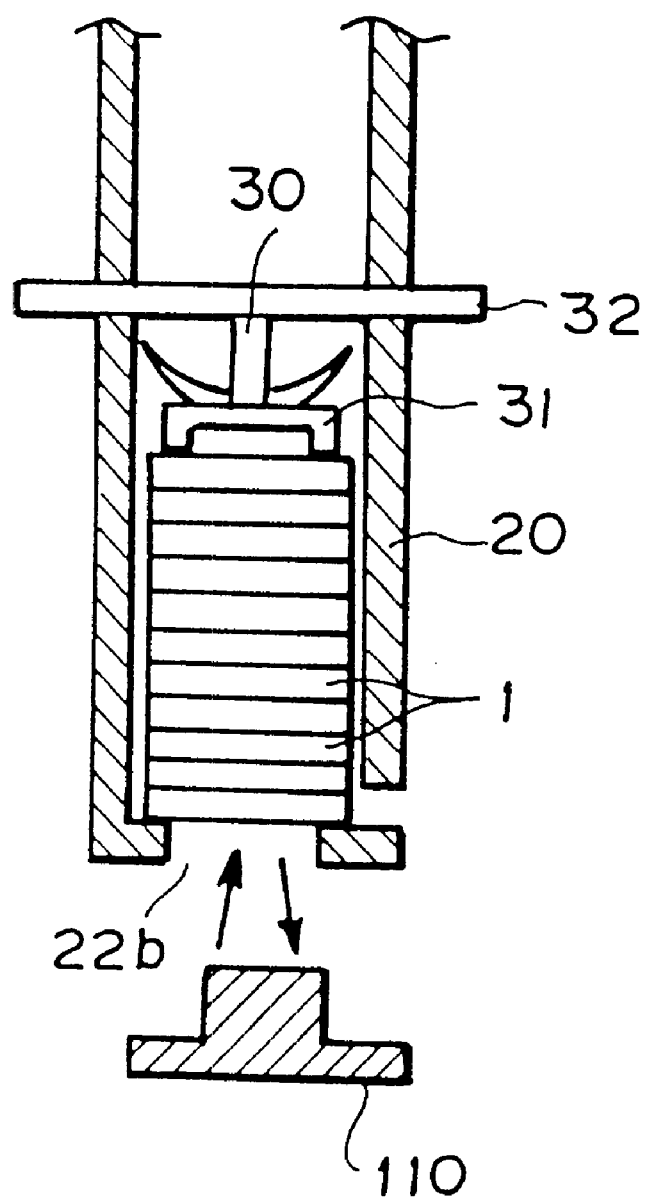
FIG. 10 is a schematic view showing an example of the film presence judging means for carrying out the method of the present invention.

A pair of reflective photosensors (reflected light receiving type photosensors) 110 are provided in the film presence judging position 102, one adapted to be opposed to the second opening 22b of one of the cartridges 20 on the inner circle and the other adapted to be opposed to the second opening 22b of one of the cartridges 20 on the outer circle. As shown in FIG. 10, the reflective photosensor 110 projects a light beam into the cartridge 20 through the second opening 22b and detects reflected light from the lower surface of the frameless chemical analysis film 1 or the lower surface of the pressing member 31 of the feed mechanism 30. The lower surface of the film 1 is substantially white and the lower surface of the pressing member 31 is colored black, that is, the former exhibits a reflectivity higher than that of the latter. Accordingly, by detecting the amount of light of the reflected light and comparing the level of the amount of the reflected light with a predetermined reference level, it can be judged whether the reflected light is from the lower surface of the film 1 or the lower surface of the pressing member 31.

When it is determined that the reflected light is from the lower surface of the film 1, there remains at least one film 1 in the cartridge 20, and when it is determined that the reflected light is from the lower surface of the pressing member 31, there remains no film 1 in the cartridge 20.

The comparison of the level of the amount of the reflected light and the reference level is performed by a comparator (not shown) and/or a software (comparison routine) and when no film remains in the cartridge 20, an alarm means such as an LED, a buzzer, a CRT display, a flat display or the like is operated to alert the operator as to an absence of film (that there remains no film in the cartridge).

It is preferred that the detection of the amount of the reflected light be effected with the films 1 (if any) in the cartridge 20 pressed flat or substantially flat by the pressing member 31 under the force of the spring 61. By effecting the detection of the amount of the reflected light in this state, the distance between the reflective photosensor 110 and the lowermost film 1 can be substantially constant, whereby the amount of reflected light from the lower surface of the film 1 can be substantially constant.

The light beam projected into the cartridge 20 may be infrared rays or ultraviolet rays as well as visible light rays.

The lower surface of the pressing member 31 may be colored in other than black so long as the difference in reflectivity between the colors of the lower surface of the film 1 and the lower surface of the pressing member 31 is sufficient.

The cartridge 20 whose stack of the films 1 has been fed in the manner described above stands by for next takeout of the film 1 so long as it is judged that there remains a film 1 in the cartridge 20 and when a film 1 is to be taken out therefrom, the cartridge 20 is moved to the film takeout position. However when it is judged that there remains no film 1 in the cartridge 20, the cartridge 20 is left there and the operations for taking out the film 1 from the cartridge 20 is abandoned. In the film takeout position, the suction pad 70 takes out the film 1 through the film takeout port 22 in the following manner.

Figure 11:
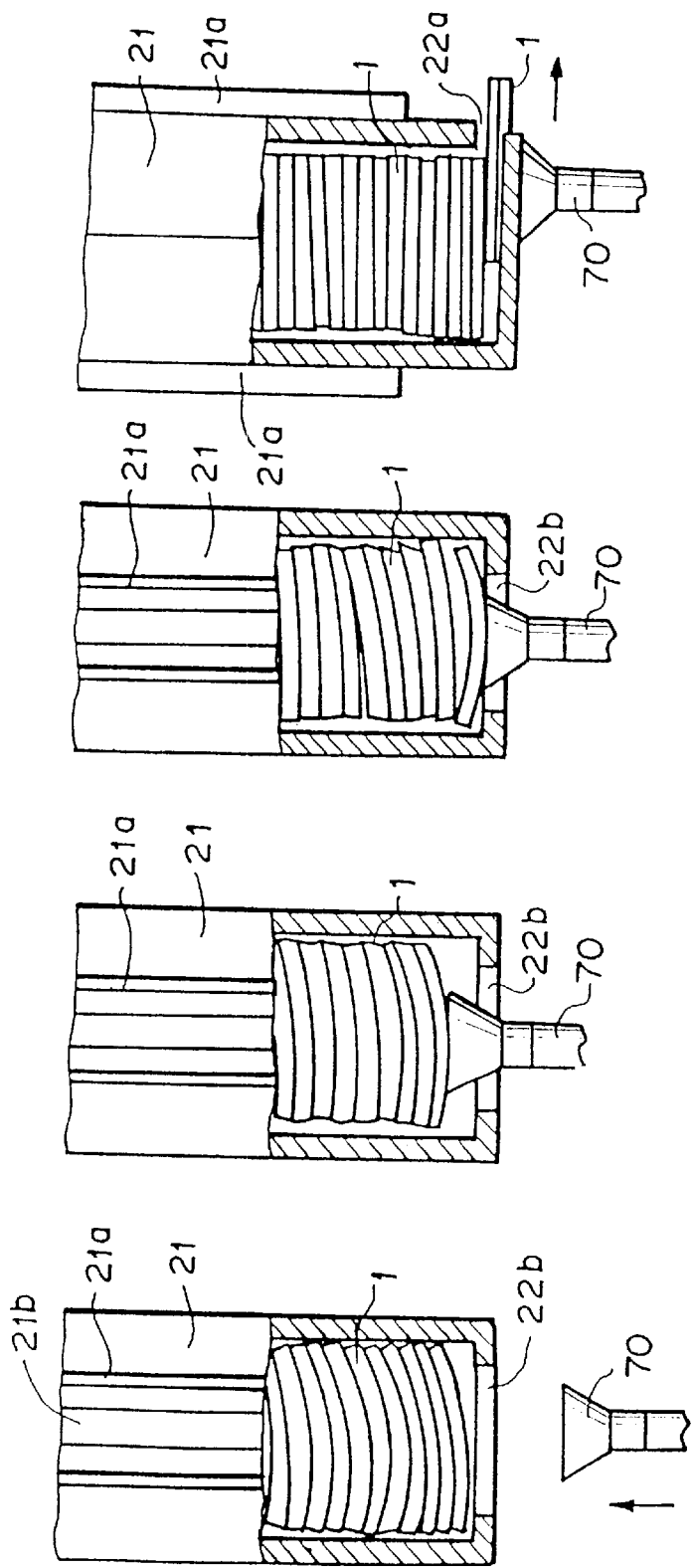
FIGS. 11A to 11D are schematic views for illustrating the procedure of taking out the film from the cartridge.

As shown in FIG. 11A, the films 1 are stacked in the cartridge 20 with each of the film chips 1 curled toward the spreading layer 4 to be convex downward and the stack is in the state where the pressing force acting on the films 1 is reduced. The suction pad 70 for taking out the film 1 is moved upward and inserted through the second opening 22b of the cartridge body 21 to be brought into abutment against the lowermost film 1 and further moved upward into closer contact with the lowermost film 1 as shown in FIG. 11B. In this position, the suction pad 70 holds the lowermost film 1 under a suction force supplied from a vacuum pump not shown.

Thereafter the suction pad 70 is moved downward holding the film 1 until both edge portions of the film 1 are brought into abutment against the edges of the second opening 22b and the film 1 is reshaped into the predetermined warped-shape convex downward as shown in FIG. 11C.

After the reshaping, the suction pad 70 is slid toward the first opening 22a holding the reshaped film 1 to take out the same through the first opening 22a as shown in FIG. 11D. After the film 1 is thus taken out, the cartridge 20 is moved to the film presence judging position 102 and the stack of the films 1 is fed toward the film takeout port 22 by the urging means 50.

The system for carrying out the method of judging presence of a frameless chemical analysis film in a cartridge need not be limited to that described above but may be variously modified. For example, the film presence judging position 102 need not be spaced from the film takeout position 101 by 180° but may be by other angle such as 30° or 45° so long as the positions 101 and 102 do not interfere with each other. Further the stack of the films 1 may be fed toward the film takeout port 22 by the urging means 50 in a position separate from the film presence judging position 102.

Further various film presence judging means may be used without limiting to that described in the embodiment described above.

Various film presence judging means for judging whether there remains a film 1 in a cartridge 20 will be described hereinbelow.

Figure 12:
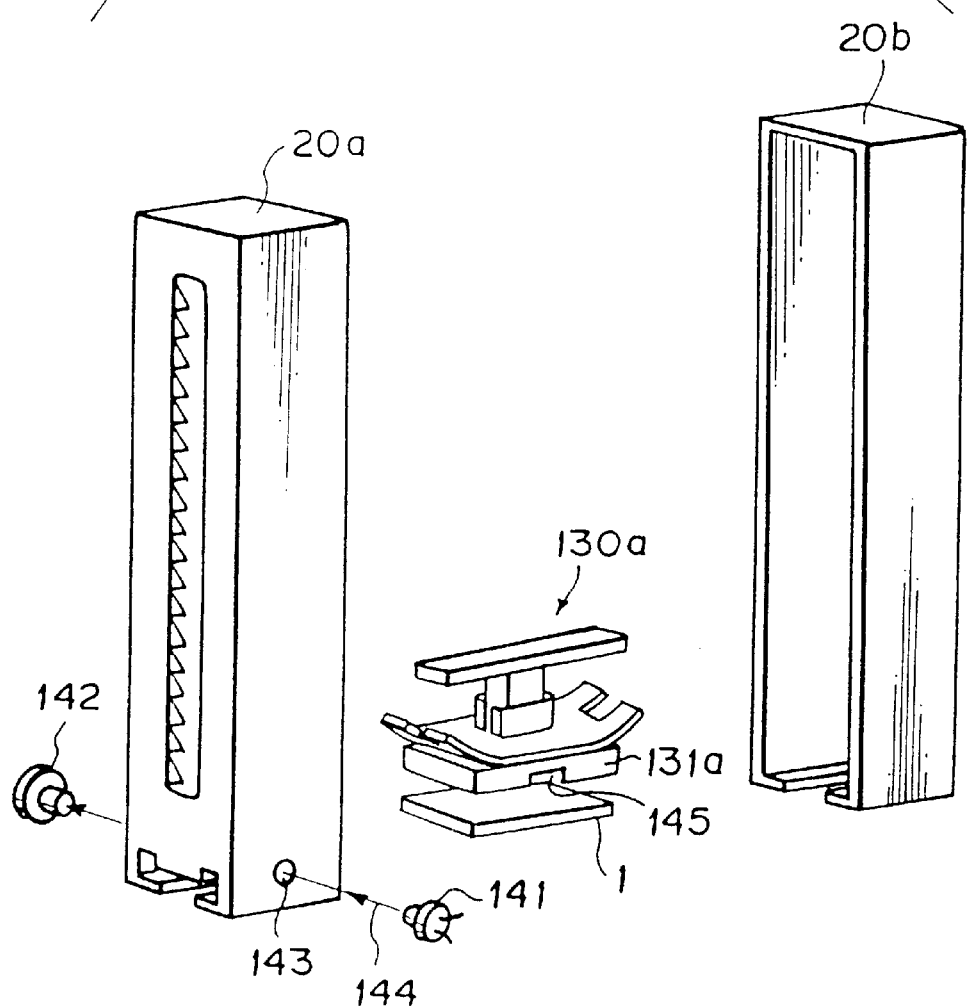
FIG. 12 is a schematic view showing another example of the film presence judging means.

In the example shown in FIG. 12, a pair of through holes 143 are provided in alignment with each other in opposed side walls of one of cartridge halves 20a and 20b and a light passage portion 145 is formed in the lower portion of a pressing member 131a so that the through holes 143 are in alignment with the lowermost film 1 when there remains one or more film 1 in the cartridge and are brought into alignment with the light passage portion 145 when all the films 1 in the cartridge are taken out. A light beam projector 141 and a photodetector 142 are disposed on opposite sides of the cartridge in alignment with each other. When there remains one or more film 1 in the cartridge, a light beam 144 projected from the light beam projector 141 is obstructed by the side edge of the lower most film 1 and is not received by the photodetector 142. On the other hand, when there remains no film 1 in the cartridge, the light beam 144 projected from the light beam projector 141 travels through the through holes 143 and the light passage portion 145 and is received by the photodetector 142. That is, when the photodetector 142 receives the light beam 144 from the light beam projector 141, it is judged that no film remains in the cartridge.

Figure 13:
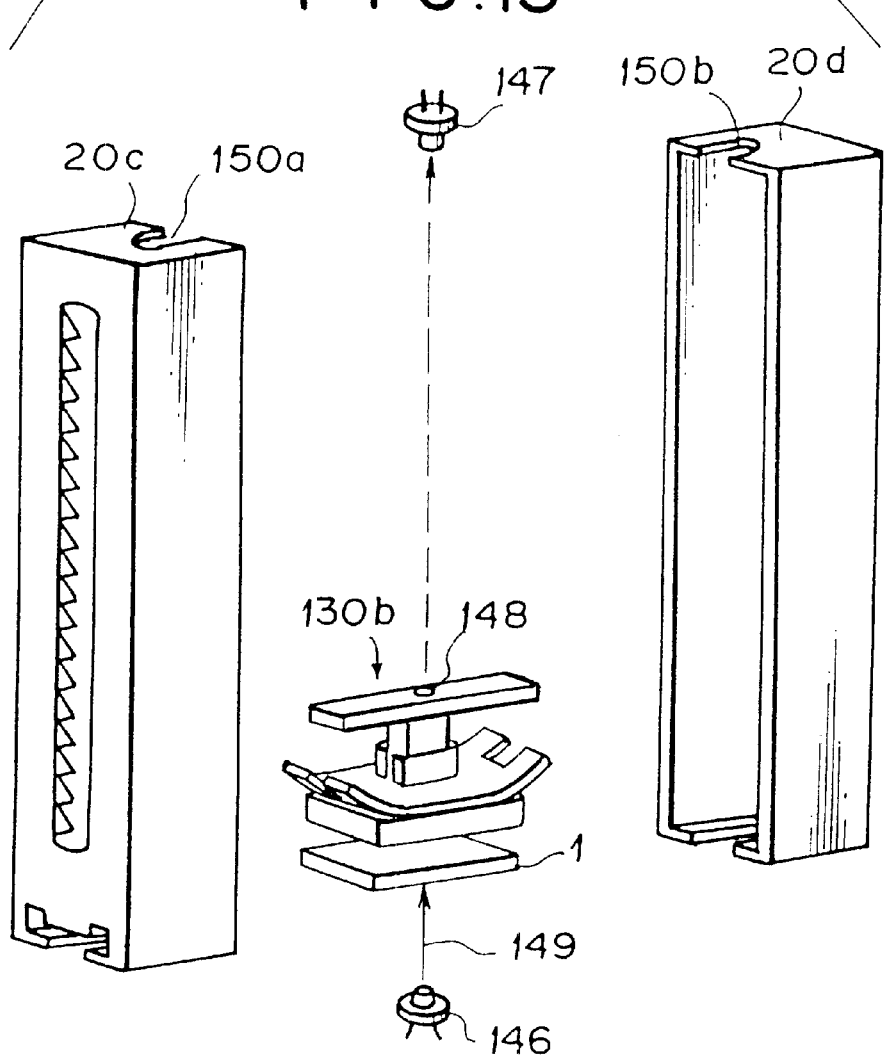
FIG. 13 is a schematic view showing still another example of the film presence judging means.

In the example shown in FIG. 13, a pair of light passage portions 150a and 150b are respectively formed in the top wall of cartridge halves 20c and 20d so that a light passage hole is formed in the center of the top wall of the cartridge when the cartridge halves 20c and 20d are mated together. A light passage portion 148 is formed in the feed mechanism 130b to extend through the feed mechanism 130b in the vertical direction in alignment with the light passage hole formed by the light passage portions 150a and 150b. A light beam projector 146 and a photodetector 147 are respectively disposed below and above the cartridge in alignment with the light passage hole, the light passage portion 148 and the second opening 22b. When there remains one or more film 1 in the cartridge, a light beam 149 projected from the light beam projector 146 is obstructed by the lower most film 1 and is not received by the photodetector 147. On the other hand, when there remains no film 1 in the cartridge, the light beam 149 projected from the light beam projector 146 travels through the second opening 22b, the light passage portion 148 and the light passage hole and is received by the photodetector 147. That is, when the photodetector 147 receives the light beam 149 from the light beam projector 146, it is judged that no film remains in the cartridge.

Figure 14:
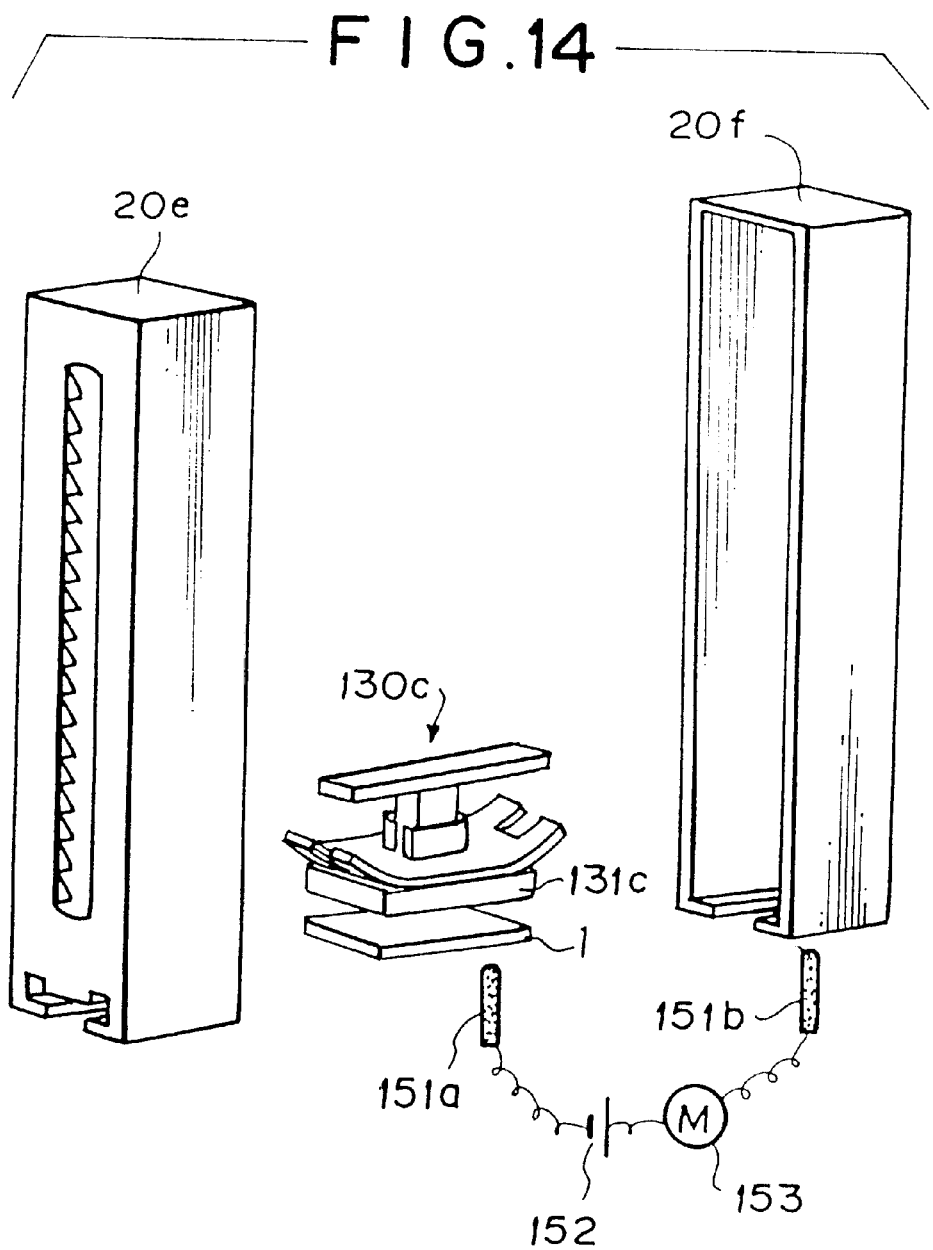
FIG. 14 is a schematic view showing still another example of the film presence judging means.

In the example shown in FIG. 14, whether there remains one or more film 1 is electrically detected. That is, the cartridge halves 20e and 20f and the pressing member 131c of the feed mechanism 130c are made of conductive material while the film 1 is made of insulating material. An electric source 152 and an electric current detecting means (e.g., an ammeter) 153 are connected between a pair of electrodes 151a and 151b. One electrode 151a is inserted into the cartridge through the second opening 22b to be pressed against the lowermost film 1 (if any) or the pressing member 131c (when no film 1 is in the cartridge) and the other electrode 151b is held in contact with the cartridge body. When one or more film 1 remains in the cartridge, no electric current flows between the electrodes 151a and 151b but when no film remains in the cartridge, the electrode 151a is brought into contact with the pressing member 131c of the feed mechanism 130c made of conductive material and an electric current flows between the electrodes 151a and 151b. Accordingly, whether there remains one or more film 1 can be detected by detecting the electric current which flows between the electrodes 151a and 151b.

The pressing member 131c of the feed mechanism 130c may be made of insulating material while the film 1 is made of conductive material so that an electric current flows between the electrodes when one or more film 1 remains in the cartridge and no current flows when no film 1 remains in the cartridge.

Otherwise, both the electrodes 151a and 151b may be inserted into the cartridge through the second opening 22b to be pressed against the lowermost film 1 (if any) or the pressing member 131c (when no film 1 is in the cartridge) so that the electrodes 151a and 151b are electrically connected with each other through the pressing member 131c when no film 1 remains in the cartridge.

Whether there remains one or more film 1 in the cartridge may be detected by detecting whether vacuum is established in the suction pad 70. That is, a through hole is formed in the pressing member in the area at which the suction pad 70 is brought into contact with the pressing member when no film 1 remains in the cartridge. When one or more film 1 remains in the cartridge, the suction pad 70 attracts the lowermost film 1 under a suction force and a vacuum is established in the suction pad 70 but when no film 1 remains in the cartridge, the suction pad 70 is brought into contact with the pressing member and vacuum is not established in the suction pad 70 even if a suction force is applied to the suction pad. Accordingly by detecting the pressure in the vacuum system by a pressure sensor such as a vacuum indicator, whether there remains one or more film 1 in the cartridge can be detected.

Further by making the pressing member of magnetic material and the film 1 and the other parts around the film 1 of non-magnetic material, whether there remains one or more film 1 in the cartridge can be detected by a magnetic detecting means.

Figure 15:
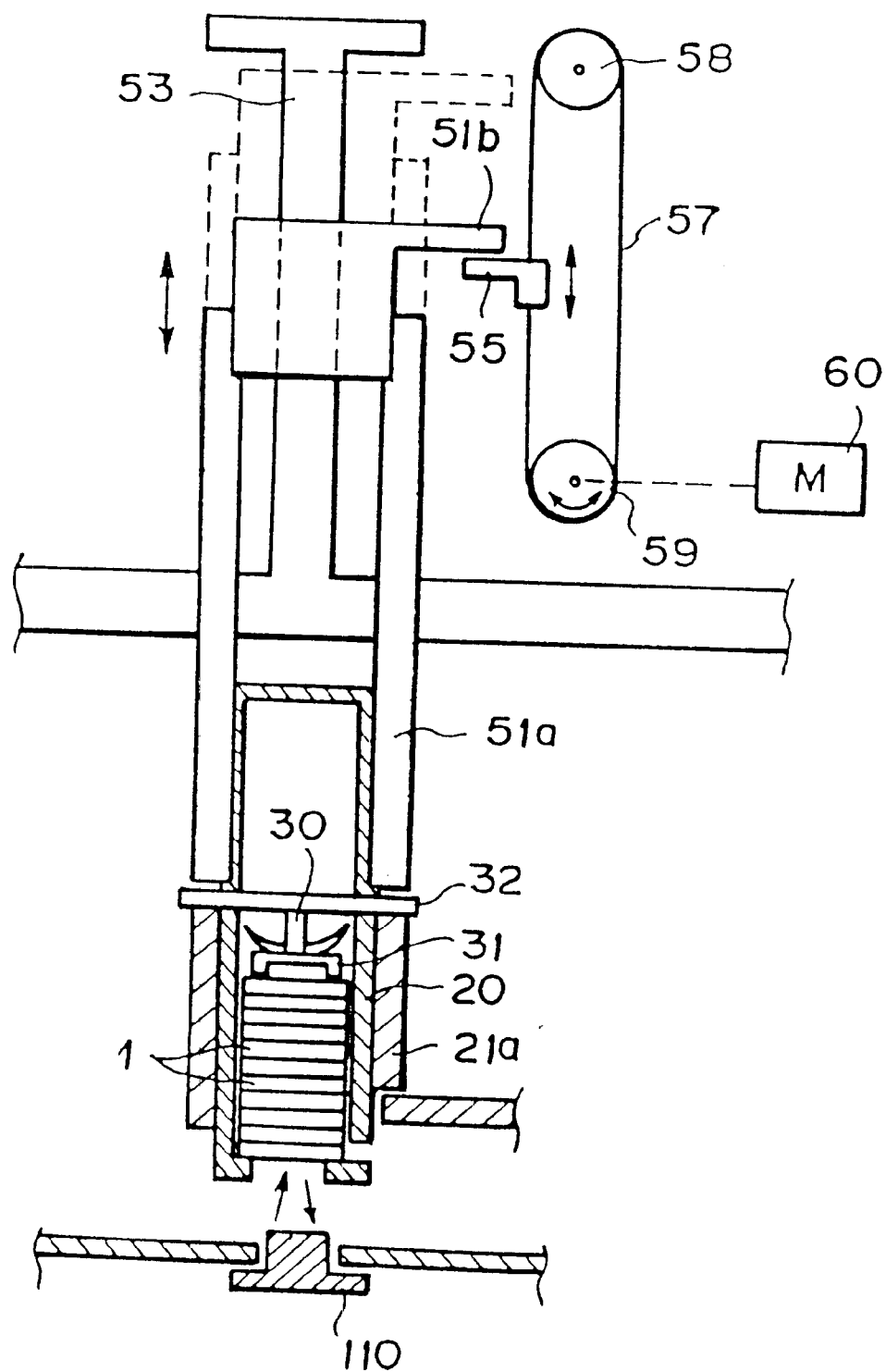
FIG. 15 is a schematic view showing a modification of the actuator member shown in FIG. 8, and FIGS. 16A and 16B are schematic views for illustrating a prior art.

FIG. 15 shows a modification of an actuator member 51 for actuating the external force receiving portion 32. The actuator member 51a shown in FIG. 15 is an elongated member extending in the vertical direction and has an weight sufficient to actuate the feed mechanism 30 under its gravity (e.g., 100 g). The actuator member 51$a$ is normally supported by the support arm 55 and when the support arm 55 is moved downward, the actuator member 51$a$ pushes downward the external force receiving portion 32 under its gravity to feed downward the feed mechanism 30 by a distance corresponding to one ratchet tooth 21$c$.

As can be understood from the description above, in accordance with the method of the present invention, whether there remains a film in the cartridge is judged in a position which is different in space from the film takeout position, and accordingly the film presence judging means can be provided independently from the film takeout means, whereby the biochemical analyzing efficiency can be improved without lowering the freedom in design of the apparatus. Further when the frameless chemical analysis films in the cartridge is taken out by means of a suction attracting means such as a suction pad, the films can be taken out without damage.

What is claimed is:

1. A method for determining a presence of a frameless dry chemical analysis film element in a cartridge in which a plurality of frameless chemical analysis film elements are stacked, comprising:

providing a film cartridge and a plurality of frameless chemical analysis film elements, at least some of said film elements being curled or warped;

placing said film elements in a stack in said cartridge;

pressing said film elements in said stack towards a film takeout port of said cartridge with an amount of force not larger than that required to completely flatten all of said frameless film elements in said stack including said film elements being curled or warped;

moving said cartridge periodically between a first position and a second position spaced from said first position;

removing said film elements through said film takeout port at said first position of said cartridge; and automatically detecting a presence of at least one of said film elements in said cartridge by passing the cartridge through a light beam, the cartridge having opposing cooperating apertures therein to allow the light beam to pass through the cartridge and impinge upon a photodetector in the absence of a film element in the cartridge or be prevented from impinging upon the photodetector by the presence of a film element in the cartridge.

* * * * *

UNITED STATES PATENT AND TRADEMARK OFFICE
CERTIFICATE OF CORRECTION

PATENT NO. : 6,468,801 B2
DATED : October 22, 2002
INVENTOR(S) : Yoshihiro Seto et al.

It is certified that error appears in the above-identified patent and that said Letters Patent is hereby corrected as shown below:

Title page,
Item [30], Foregin Applications Priority Data, should read
-- March 11, 1994 (JP) 6-40194 --

Signed and Sealed this

Twenty-seventh Day of July, 2004

JON W. DUDAS
*Acting Director of the United States Patent and Trademark Office*